United States Patent [19]

Jessel, Jr. et al.

[11] Plant 4,786

[45] Nov. 3, 1981

[54] CHRYSANTHEMUM PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 175,752

[22] Filed: Aug. 5, 1980

[51] Int. Cl.[3] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Koch

[57] ABSTRACT

A chrysanthemum cultivar known by the cultivar name Cheers and characterized as to uniqueness by the combined characteristics of flat capitulum form; daisy capitulum type; white ray floret color; diameter across face of capitulum ranging from 95 to 105 mm. at maturity; uniform seven week photoperiodic flowering response to short days; long peduncle length, ranging from 175 to 220 mm.; medium plant height when grown as a single stem cut spray; and semi-upright branching pattern.

3 Drawing Figures

The present invention comprises a new and distinct cultivar of *Chrysanthemum morifolium*, Ramat., hereinafter referred to by the cultivar name Cheers.

Cheers is a product of a planned breeding program which had the objective of creating new chrysanthemum cultivars with daisy capitulum type, white ray floret color, eight week flowering response, and with the ability to produce commercially acceptable quality in year round cut mum programs. Such traits in combination were not present in previously available commerical cultivars.

Cheers was originated from a hybridization made in a controlled breeding program in Barberton, Ohio in 1975. The female parent was Superstar, disclosed in U.S. Plant Pat. No. 4,299. The male parent of Cheers was an unnamed white anemone seedling (#73194015) originated by the present inventors from a hybridization of Wedgewood, disclosed in U.S. Plant Pat. No. 3,598, and Topflight (unpatented; commercially available). Cheers was discovered and selected as one flowering plant within the progeny of the stated parentage by Walter H. Jessel, Jr. and William E. Duffett on Nov. 12, 1976 in a controlled environment in Barberton, Ohio.

The first act of asexual reproduction of Cheers was accomplished when vegetative cuttings were taken from the initial selection in January, 1977 in a controlled environment in Barberton, Ohio by a technician working under formulations established and supervised by Walter H. Jessel, Jr. and William E. Duffett. Horticultural examination of selected units initiated Nov. 7, 1977 has demonstrated that the combination of characteristics as herein disclosed for Cheers are firmly fixed and are retained through successive generations of asexual reproduction.

Cheers has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Cheers which in combination distinguish this chrysanthemum as a new and distinct cultivar:

(1) flat capitulum form, (2) daisy capitulum type, (3) white ray floret color, (4) yellow-green (immature) to yellow (mature) disc floret color, (5) diameter across face of capitulum ranging from 95 to 105 mm. at maturity, (6) uniform seven week photoperiodic flowering response to short days, (7) long peduncle length, ranging from 175 to 220 mm., (8) medium plant height (requiring from one to two long days weeks prior to short days to attain a flowered plant height of 65 to 75 cm. for May through October flowerings), and (9) semi-upright branching pattern.

Of the many commercial cultivars known to the present inventors, the most similar in comparison to Cheers is White Marble (unpatented). Reference is made to attached Chart A which compares certain characteristics of Cheers to those same characteristics of White Marble. In general comparison to White Marble, Cheers has larger diameter across face of capitulum and shorter flowering response period. The ray floret color, capitulum form, capitulum type, plant height and peduncle length of Cheers are similar to those same characteristics of White Marble.

The accompanying photographic drawings show typical inflorescence and foliage characteristics of Cheers with colors being as nearly true as possible with illustrations of this type. Sheet 1 is a color photograph of Cheers. Sheet 2 is a black and white photograph showing three views of the inflorescence of Cheers. Sheet 3 is a black and white photograph showing the foliage of Cheers at three stages of growth.

In the following description, color references are made to the Royal Horticultural Society (R.H.S.) Color Chart. The color values were determined between 1:30 and 2:00 P.M. on Sept. 25, 1979 under 150 foot-candle light intensity at Salinas, Calif.

Classification:

*Botanical.*—*Chrysanthemum morifolium,* Ramat., cv Cheers.

*Commercial.*—Cut daisy spray chrysanthemum.

I. INFLORESCENCE

A. Capitulum (see sheets 1 and 2 of drawings):

*Form.*—Flat.

*Type.*—Daisy.

*Diameter across face.*—95 to 105 mm.

B. Corolla of ray florets:

*General tonality (from a distance of three meters).*—White, 155-D.

*Color (abaxial).*—155-D.

*Color (adaxial).*—155-D.

C. Corolla of disc florets:

*Color (abaxial).*—Approximately 144-A (immature) to 14-A (mature).

D. Reproductive organs:

*Androecium.*—Present disc florets only; scant to numerous; moderate pollen.

*Gynoecium.*—Present both ray and disc florets.

PLANT

A. General appearance:

*Branching pattern.*—Semi-upright.

*Height.*—Medium, 60 to 70 cm. given no long days for May through October flowerings.

B. Foliage (see sheet 3):

*Color (abaxial).*—Approximately 139-A but more greyed.

*Color (adaxial).*—Approximately 137-C but more greyed.

*Shape.*—Moderately lobed and deeply serrated.

CHART A

COMPARISON OF CHEERS AND WHITE MARBLE

| CULTIVAR | RAY FLORET COLOR | CAPITULUM FORM AND TYPE | PLANT HEIGHT |
|---|---|---|---|
| Cheers | White | Flat Daisy | Medium |
| White Marble | White | Flat Daisy | Medium |

| CULTIVAR | DIAMETER ACROSS FACE OF CAPITULUM | FLOWERING RESPONSE | PEDUNCLE LENGTH |
|---|---|---|---|
| Cheers | 95 to 105 mm. | 7 week | Long, 175 to 220 mm. |
| White Marble | 70 to 85 mm. | 9 week | Long, 180 to 250 mm. |

COMPARISONS MADE OF PLANTS GROWN AS SINGLE STEM CUT SPRAYS IN SALINAS, CALIFORNIA

We claim:

1. A new and distinct cultivar of *Chrysanthemum morifolium,* Ramat., plant known by the cultivar name Cheers and particularly characterized as to uniqueness, as herein described and illustrated, by the combined characteristics of flat capitulum form; daisy capitulum type; white ray floret color; diameter across face of capitulum ranging from 95 to 105 mm. at maturity; uniform seven week photoperiodic flowering response to short days; long peduncle length; medium plant height when grown as a single stem cut spray; and semi-upright branching pattern.

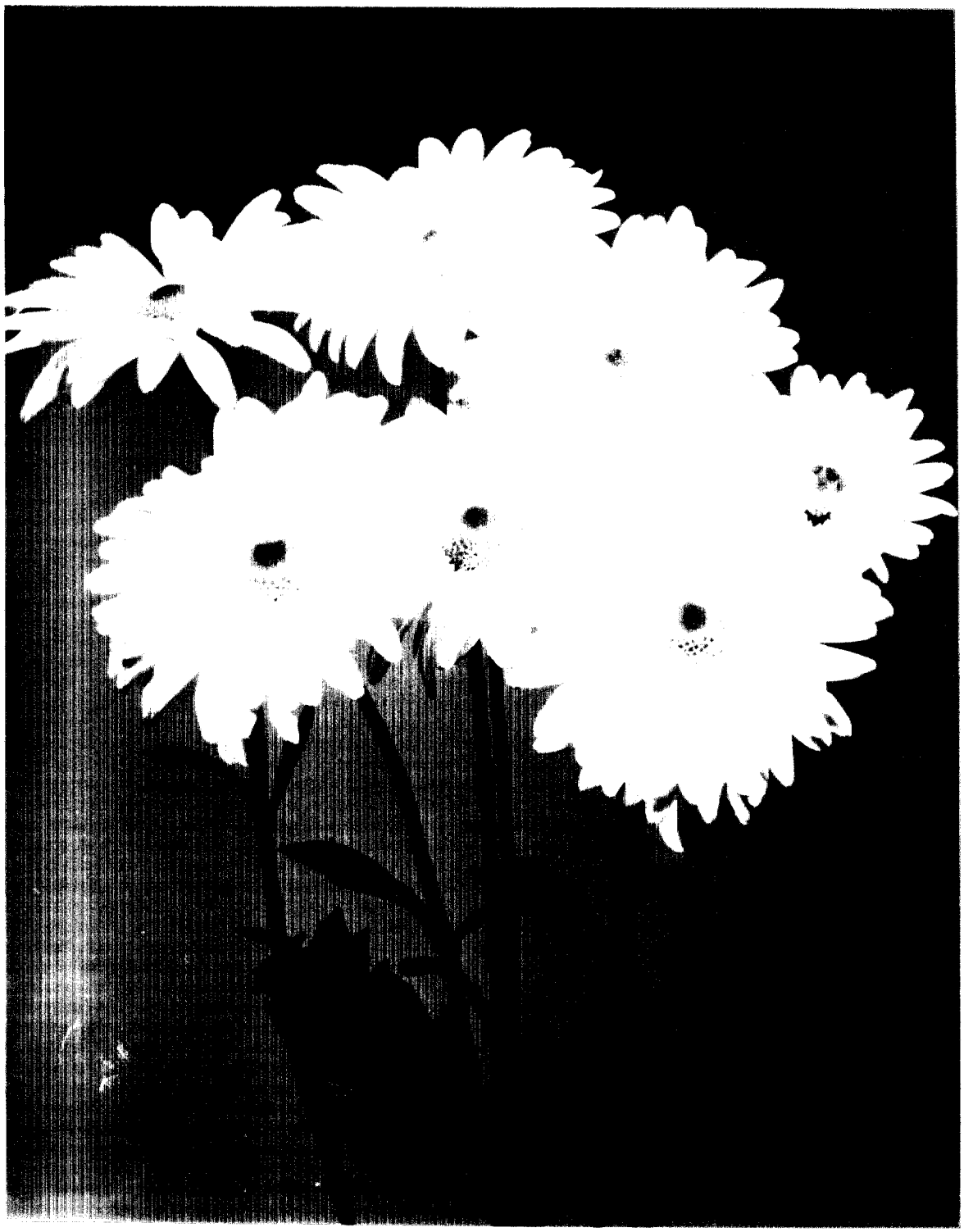

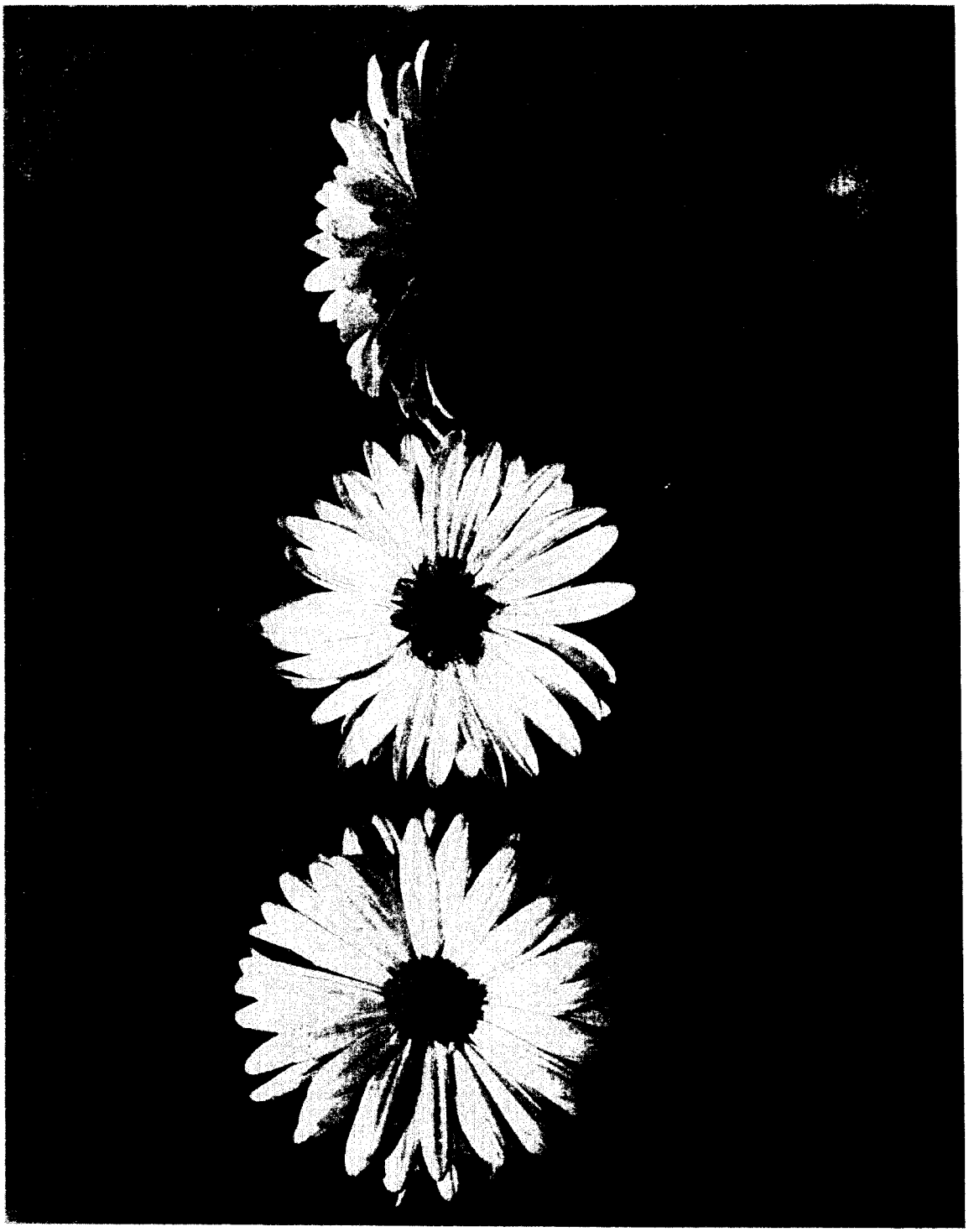

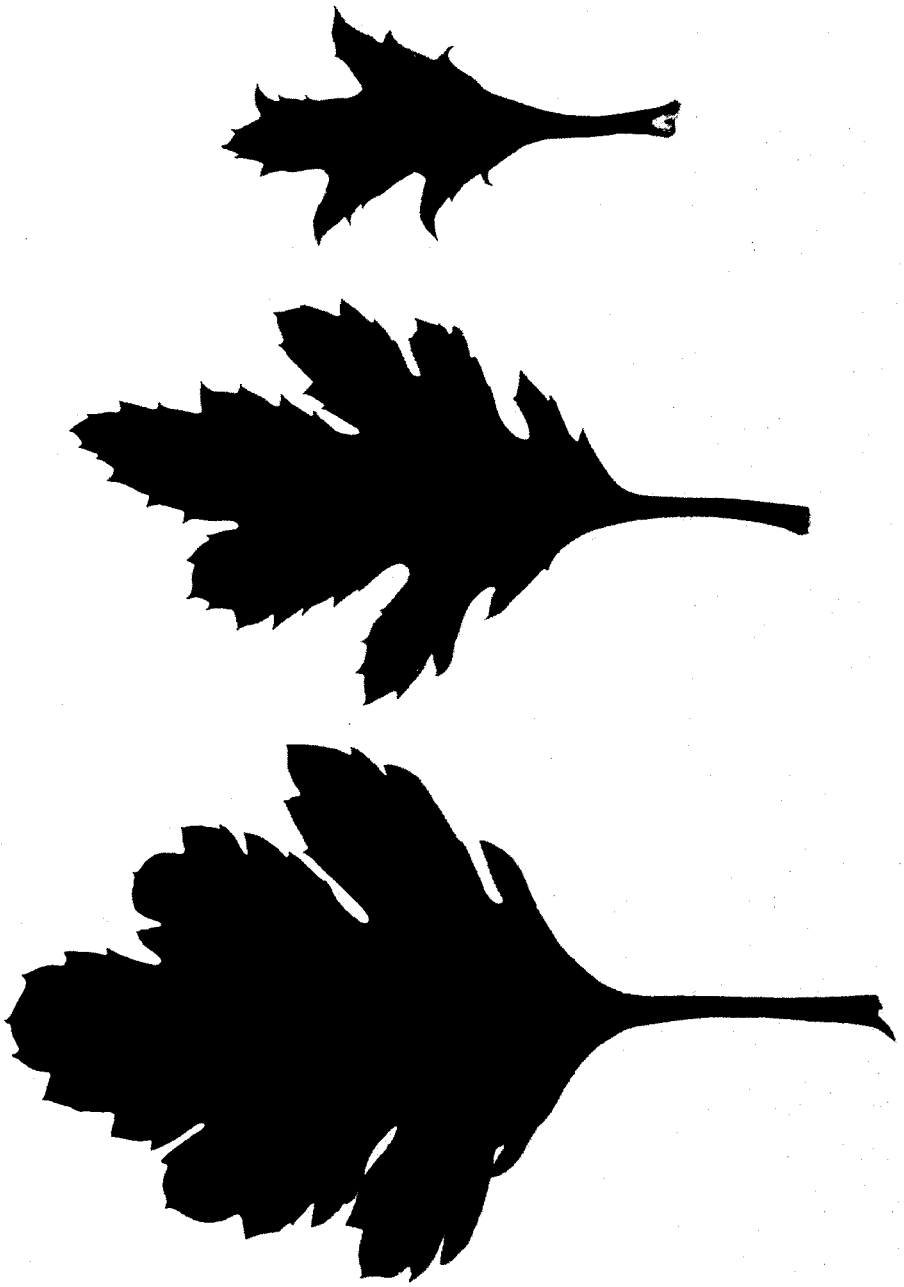

* * * * *